(12) United States Patent
Carr et al.

(10) Patent No.: US 7,212,693 B2
(45) Date of Patent: May 1, 2007

(54) OPTICAL SUBSTANCE ANALYZER

(75) Inventors: Dustin W. Carr, Albuquerque, NM (US); Ho Bun Chan, Gainesville, FL (US); Alex T. Tran, Madison, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 163 days.

(21) Appl. No.: 10/743,253

(22) Filed: Dec. 22, 2003
(Under 37 CFR 1.47)

(65) Prior Publication Data
US 2005/0135723 A1    Jun. 23, 2005

(51) Int. Cl.
*G02B 6/00*    (2006.01)

(52) U.S. Cl. .......................................... 385/12; 385/37
(58) Field of Classification Search ................ 385/12, 385/37
See application file for complete search history.

(56) References Cited

U.S. PATENT DOCUMENTS

| 4,815,843 | A | 3/1989 | Tiefenthaler et al. | 356/128 |
| 5,864,641 | A | 1/1999 | Murphy et al. | 385/12 |
| 6,903,815 | B2 * | 6/2005 | Uchiyama et al. | 356/305 |
| 2003/0092034 | A1 * | 5/2003 | Cooper et al. | 435/6 |

OTHER PUBLICATIONS

"Label-Free Biosensor Using an Optical Waveguide With Induced Bragg Grating of Variable Strength," by Dotsen ko, A.V. et al. Sensors and Actuators B 94, Elsevier Sequola S.A., Lausanne, CH, XP004438564, ISSN: 0925-4005, vol. 94, No. 1, Aug. 15, 2003, pp. 116-121.

"Multiplexing Capabilities Of A Solid State Interrogator For Spectrally Encoded Sensors," by Willshire, A.J. et al., Proceedings of IEEE Sensors 2003, 2nd IEEE International Conference on Sensors, Toronto, Canada, Oct. 22-24, IEEE International Conference on Sensors, New York, NY: IEEE US, vol. 2 or 2 Conf. 2, Oct. 22, 2003, XP010691062, ISBN: 0-7803-8133-5, pp. 1016-1020 vol. 12.

"An Integrated Optical Bragg-Reflector Used As A Chemo-Optical Sensor," Veldhus, G.J. et al., Pure and Applied Optics, Bristol, GB, vol. 7, No. 1, Jan. 1998, XP002087839, ISSN: 0963-9659, pp. L23-L26.

"Integrated: Optical Mach-Zehnder Biosensor," by B.J. Luff, et al., Journal of Lightwave Technology, 0733-8724/98 IEEE, vol. 16, No. 4, Apr. 1998, pp. 583-592.

"Sensitive Disk Resonator Photonic Blosensor," by Robert W. Boyd and John E. Heebner, Applied Optics, vol. 40, No. 31, Nov. 2001, pp. 5742-5747.

* cited by examiner

*Primary Examiner*—Jennifer Doan

(57) ABSTRACT

A portable waveguide sensor having one or more gratings. In one embodiment, the sensor has a waveguide, wherein a plurality of grooves imprinted onto the waveguide form a Bragg grating. The surface of the grooves has a functional layer adapted to bind a substance of interest, e.g., a biological pathogen. When the pathogen binds to the functional layer, the binding shifts the spectral reflection band corresponding to the Bragg grating such that a probe light previously reflected by the grating now passes through the grating, thereby indicating the presence of the pathogen. In another embodiment, the sensor has a Mach-Zehnder interferometer (MZI), one arm of which has a resonator formed by two Bragg gratings. The surface of the resonator between the gratings has a functional layer whereas the Bragg gratings themselves do not have such a layer.

39 Claims, 4 Drawing Sheets

OPTICAL SUBSTANCE ANALYZER

BACKGROUND OF THE INVENTION

1. Field of the Invention

The present invention relates to sensors and, more specifically, to optical devices for detecting chemical and biological substances.

2. Description of the Related Art

Substance analyzers are used in environmental monitoring, industrial process control, and medical, analytical, and military applications. For example, biological pathogens such as salmonella are often present in meat and poultry products. Since exposure to these pathogens is a health hazard, low concentrations, typically trace amounts, need to be detected quickly and reliably.

In an analytical laboratory, specialized techniques such as mass spectrometry, chromatography, electro-chemical analysis, immunoassays, etc., are readily available to detect various chemical and biological substances (i.e., analytes) with great sensitivity and specificity. However, the available techniques are often time-consuming, labor-intensive, and/or relatively expensive. In addition, devices implementing these techniques are not adapted for portable use, nor are they adapted for use outside the laboratory.

SUMMARY OF THE INVENTION

Problems in the prior art are addressed, in accordance with the principles of the present invention, by a portable waveguide sensor having one or more gratings adapted to cause a change in the optical characteristics of the sensor in the presence of a particular substance of interest, e.g., a biological pathogen. In one embodiment, the sensor has a waveguide, wherein a plurality of grooves imprinted onto the waveguide form a Bragg grating. The surface of the grooves has a functional layer adapted to bind the pathogen. When the pathogen binds to the functional layer, the binding shifts the spectral reflection band corresponding to the Bragg grating such that a probe light previously reflected by the grating now passes through the grating, thereby indicating the presence of the pathogen. In another embodiment, the sensor has a Mach-Zehnder interferometer (MZI), one arm of which has a resonator formed by two Bragg gratings. The surface of the resonator between the gratings has a functional layer whereas the Bragg gratings themselves do not have such a layer. Due to multiple reflections within the resonator, light coupled into the MZI interacts with the bound pathogen over a relatively large effective propagation length, which results in a relatively large differential phase shift and therefore advantageously high sensitivity to the pathogen.

DETAILED DESCRIPTION

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments.

Figure 1:
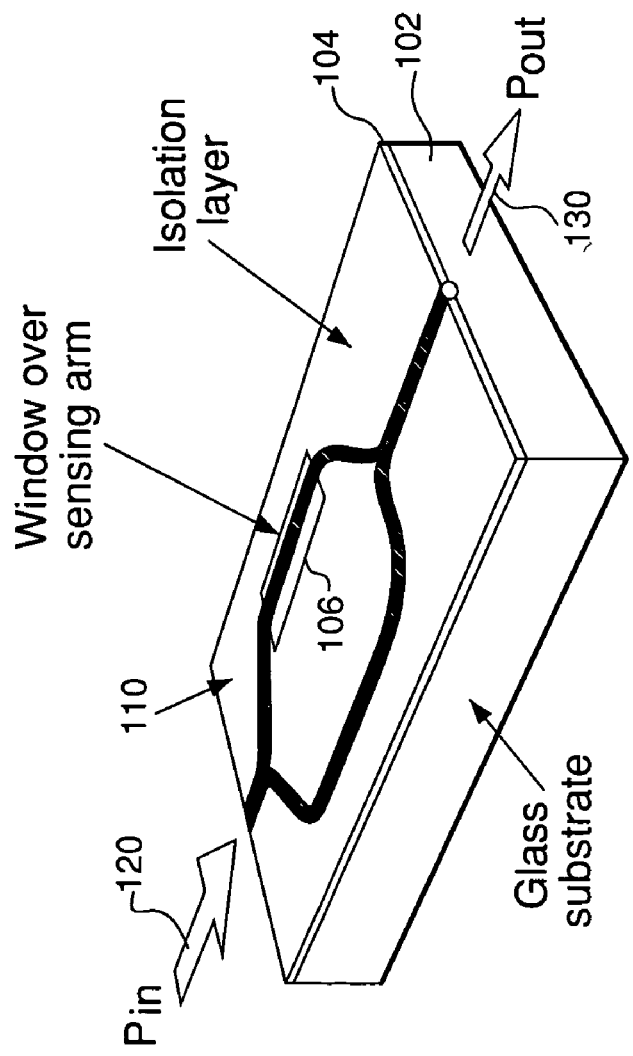
FIG. 1 shows a perspective three-dimensional view of a prior-art optical sensor.

FIG. 1 shows a perspective three-dimensional view of a prior-art optical sensor 100 disclosed in an article by B. J. Luff, et al., published in J. Lightwave Technology, 1998, Vol. 16, No. 4, p. 583, the teachings of which are incorporated herein by reference. Sensor 100 is a planar waveguide device having a Mach-Zehnder interferometer (MZI) 110 formed on a glass substrate 102. An isolation layer 104 that covers MZI 110 has an opening 106, which exposes one arm of the MZI to the environment, while keeping the other arm protected from such exposure. An optical input beam 120 applied to sensor 100 is split into two beam portions as it propagates through MZI 110, which beam portions then recombine at the output of the MZI to produce an optical output beam 130. The intensity of beam 130 depends on the differential phase shift between the beam portions at the recombination point. For example, when the differential phase shift is about $2\pi k$, where k is an integer, the beam portions interfere constructively, which causes beam 130 to have a relatively high intensity. On the other hand, when the differential phase shift is about $(2k+1)\pi$, the beam portions interfere destructively, which causes beam 130 to have a relatively low intensity.

To enable detection of a chemical or biological substance of interest, hereafter termed the "analyte," the surface of the exposed MZI arm within opening 106 is modified with a functional layer, which facilitates adsorption of the analyte onto the surface. Subsequently, when sensor 100 is exposed to the analyte, the analyte binds to the functional layer, thereby changing the arm's waveguide properties. This change alters the differential phase shift and, as a result, produces a corresponding intensity change of beam 130, which, upon detection, can be related to the presence of the analyte in the environment. However, one problem with sensor 100 is that its sensitivity may be relatively low. This is mostly due to the fact that light coupled into the exposed arm interacts with the adsorbed analyte by way of the evanescent field. Since the evanescent field is relatively weak, a relatively large interaction length is required to produce a detectable intensity change, which results in disadvantageously large and/or impractical MZI structures.

Figure 2A:
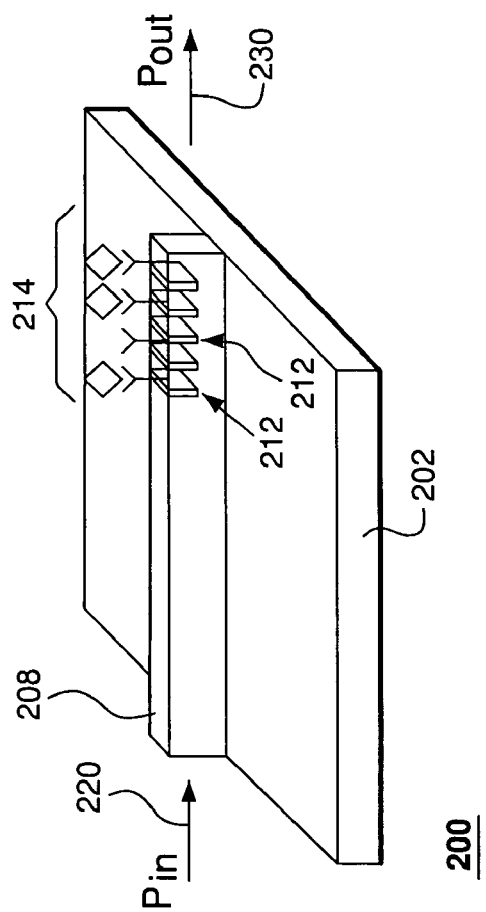
FIGS. 2A–B show an optical sensor according to one embodiment of the present invention.
Figure 2B:
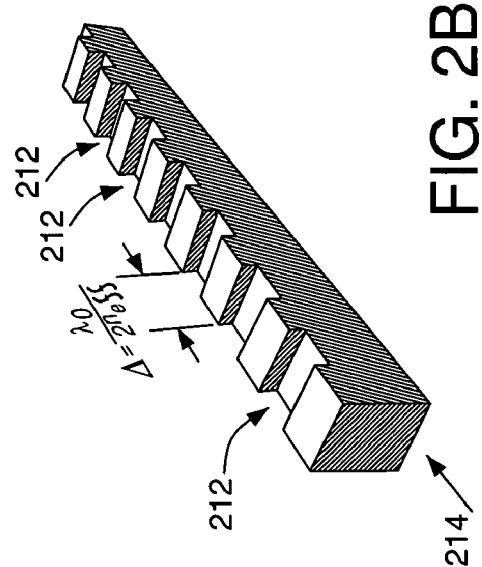

FIGS. 2A–B show an optical sensor 200 according to one embodiment of the present invention. More specifically, FIG. 2A shows a perspective three-dimensional view of sensor 200, and FIG. 2B is an enlarged view of a grooved portion of that sensor. Sensor 200 is a planar waveguide device having a waveguide 208 formed on a substrate 202. Waveguide 208 has a plurality of grooves 212, which form an integrated Bragg grating 214. As known in the art, one property of a Bragg grating is that it can reflect light corresponding to a relatively narrow spectral band while transmitting all other light. For example, grating 214 can be fabricated to have a reflection band with a center wavelength of $\lambda_0$ and a spectral width of $\Delta\lambda$, where the spectral width is the wavelength difference between the band points having one half of the reflectivity corresponding to the center wavelength. In one implementation, $\lambda_0$ and $\Delta\lambda$ are about 1550 nm and 0.1 nm, respectively, and the reflectivity at $\lambda_0$, is about 100%.

To enable analyte detection, the surface of grooves 212 is modified with a functional layer similar to that of sensor 100. In FIG. 2A, the functional layer is schematically illustrated by the Y-shaped symbols connected to grooves 212. When sensor 200 is exposed to the analyte (schematically illustrated by diamonds in FIG. 2A), the analyte binds to the functional layer, thereby changing optical properties of grating 214. For example, for a periodic groove structure having a period of $\Lambda$ (see FIG. 2B), the center wavelength is given by the following equation:

$$\lambda_0 = 2\Lambda n_{\it eff} \quad (1)$$

where $n_{\it eff}$ is the effective index of refraction corresponding to grating 214. When the analyte binds to the functional layer, it changes $n_{\it eff}$ and therefore $\lambda_0$. Suppose that an optical input beam 220 coupled into waveguide 208 has wavelength $\lambda'_0$ corresponding to the center wavelength of grating 214 in the absence of the analyte. Then, an optical output beam 230 will have a very low intensity due to the Bragg reflection. However, when sensor 200 is exposed to the analyte, the analyte binding changes $n_{\it eff}$ and shifts the center wavelength to $\lambda''_0$. This shift reduces the grating reflectivity at $\lambda'_0$, which causes the intensity of beam 230 to increase, thereby indicating the presence of the analyte in the environment. Advantageously, the sensitivity of sensor 200 is improved compared to the sensitivity of device 100. The improvement is mostly due to the corrugated profile of grating 214, which increases the interaction cross-section of the probe light with the bound analyte in sensor 200 compared to that in the evanescent-field-limited structure of sensor 100.

Figure 3:
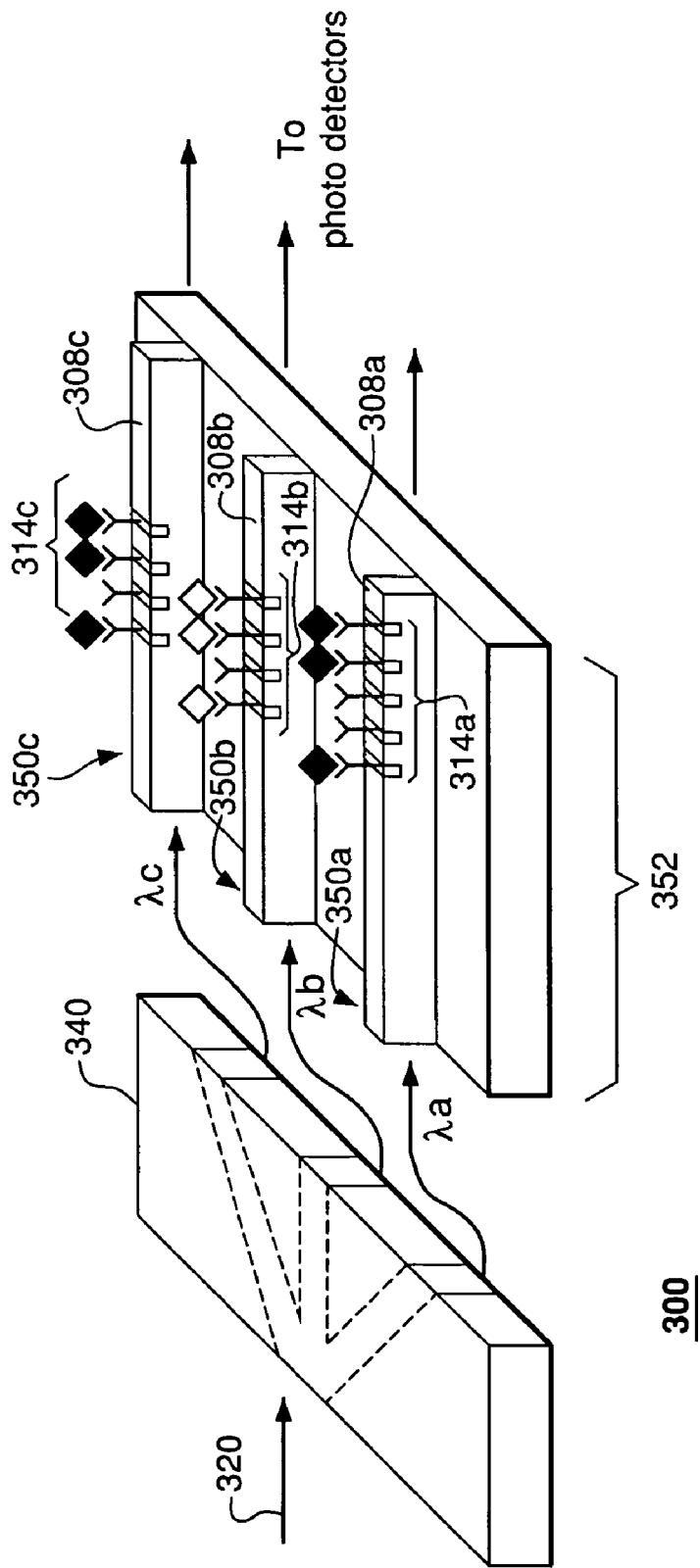
FIG. 3 shows an optical sensing system having an array of sensors similar to the sensor shown in FIG. 2 according to one embodiment of the present invention.

FIG. 3 shows an optical sensing system 300 according to one embodiment of the present invention. System 300 has an arrayed waveguide grating (AWG) 340, whose output ports are coupled to a sensor 352. Sensor 352 is an arrayed sensor having three sensors 350a–c, each of which is similar to sensor 200 of FIG. 2. However, sensors 350a–c differ from each other in that (1) each sensor has a different center wavelength (i.e., $\lambda_a$, $\lambda_b$, and $\lambda_c$, respectively) and (2) each sensor has a different functional layer adapted to bind a different analyte. Functionalization of surface layers to enable analyte-specific conjugation is well known in the bio-technological arts and is described, for example, in a book by G. T. Hermanson, "Bioconjugate Techniques," Academic Press, San Diego, 1996, the teachings of which are incorporated herein by reference. Therefore, system 300 is adapted to detect three different analytes. One skilled in the art will appreciate that a sensing system adapted to detect two or four or more different analytes may be similarly designed. In a preferred embodiment, AWG 340 and sensor 352 are implemented in an integrated waveguide circuit.

In operation, a multiplexed optical input beam 320 having wavelengths $\lambda_a$, $\lambda_b$, and $\lambda_c$ is applied to AWG 340. Each component is then routed to the appropriate output port and coupled into the corresponding waveguide 308, where it impinges upon Bragg grating 314. Light passed through the gratings is measured using an array of photo-detectors (not shown) to sense the presence of the different analytes, e.g., as described above for sensor 200.

Figures 4A, 4B:
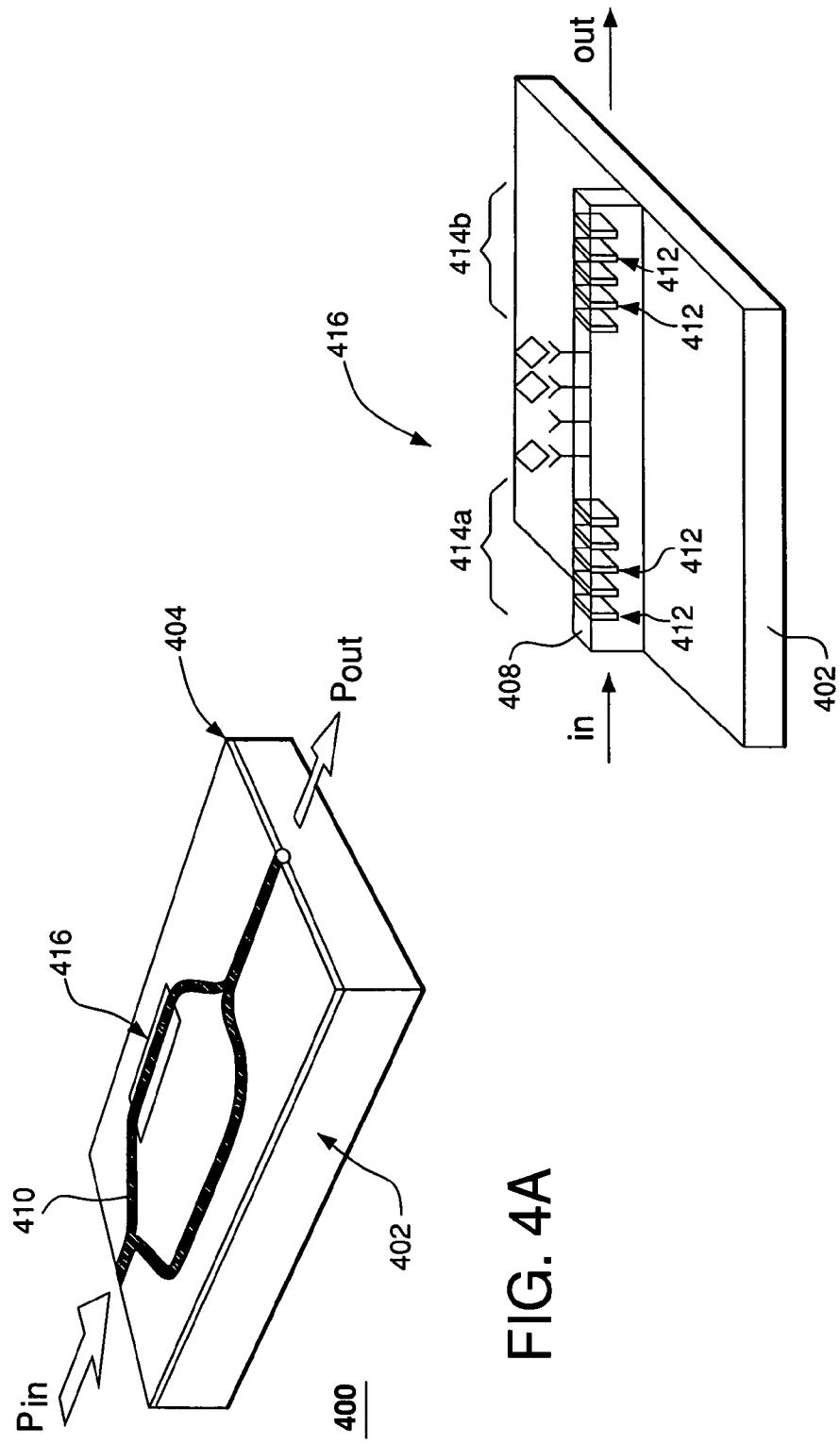
FIGS. 4A–B show an optical sensor according to another embodiment of the present invention.

FIGS. 4A–B show an optical sensor 400 according to another embodiment of the present invention. More specifically, FIG. 4A shows a perspective three-dimensional view of sensor 400, and FIG. 4B shows an enlarged view of an optical resonator 416 of that sensor. Sensor 400 has a Mach-Zehnder interferometer (MZI) 410 formed on a substrate 402 and covered by an isolation layer 404 similar to MZI 110 of sensor 100 (FIG. 1). However, one difference between MZI 410 and MZI 110 is that the exposed arm of MZI 410 has two Bragg gratings 414a–b, which form resonator 416. Each grating 414 is formed with grooves 412 imprinted onto a waveguide 408 as shown in FIG. 4B. The reflectivity of each Bragg grating is appropriately chosen to couple light in and out of resonator 416 and to generate multiple round trips of the light within the resonator.

A section of waveguide 408 between gratings 414a–b has a functional layer indicated in FIG. 4B by the Y-shaped symbols. In a preferred implementation, grooves 412 do not have such a layer. This ensures that the resonator's optical properties are not substantially altered by the exposure to the analyte. Resonator 416 thus mostly serves to increase the effective interaction length of light within the exposed arm of MZI 410 with the bound analyte (schematically illustrated by diamonds in FIG. 4B). Due to the increased interaction length, the differential phase shift generated in MZI 410 is significantly greater than that in a similarly sized MZI 110 (FIG. 1). Therefore, the sensitivity of sensor 400 is advantageously improved compared to the sensitivity of sensor 100.

While this invention has been described with reference to illustrative embodiments, this description is not intended to be construed in a limiting sense. Although Bragg gratings of the invention are described as being implemented with grooves imprinted onto a waveguide, other grating implementations known in the art may similarly be used. The gratings may have reflection bands that have different center wavelengths and/or different shapes. Waveguide resonators of the invention may be implemented using different light-reflecting structures as known in the art. Various modifications of the described embodiments, as well as other embodiments of the invention, which are apparent to persons skilled in the art to which the invention pertains are deemed to lie within the principle and scope of the invention as expressed in the following claims.

Although the steps in the following method claims, if any, are recited in a particular sequence with corresponding labeling, unless the claim recitations otherwise imply a particular sequence for implementing some or all of those steps, those steps are not necessarily intended to be limited to being implemented in that particular sequence.

What is claimed is:

1. A device, comprising an optical waveguide having a first grating, wherein:
    at least a portion of the waveguide has a functional layer adapted to bind an analyte;
    a plurality of grooves in the optical waveguide form the first grating;
    at least some of the grooves are covered by the functional layer;
    when the analyte binds to the functional layer, the binding changes optical characteristics of the waveguide;
    the first grating has an optical reflection band characterized by a center wavelength; and
    the binding shifts the center wavelength.

2. The device of claim 1, comprising one or more additional optical waveguides, each having a grating, wherein:
    each grating has an optical reflection band characterized by a center wavelength; and
    at least two gratings have different reflection bands.

3. The device of claim 2, further comprising an arrayed waveguide grating (AWG) having an input port and two or more output ports coupled to the two or more optical waveguides, wherein, for each optical waveguide, the AWG is adapted to route light having a corresponding center wavelength from the input port to the output port coupled to said optical waveguide.

4. The device of claim 3, wherein the AWG and the two or more optical waveguides are implemented in a single integrated device.

5. The device of claim 2, wherein at least two optical waveguides have different functional layers adapted to bind different analytes.

6. The device of claim 1, comprising a Mach-Zehnder interferometer (MZI) having two arms, wherein one arm includes the optical waveguide.

7. The device of claim 6, wherein:
the optical waveguide has a second grating; and
the first and second gratings form an optical resonator.

8. The device of claim 7, wherein:
a section of the optical waveguide between the first and second gratings has the functional layer; and
the binding changes a differential phase shift in the MZI.

9. The device of claim 1, wherein the first grating is a Bragg grating.

10. A method for detecting an analyte, comprising: transmitting light through an optical waveguide having a first grating; and measuring the transmitted light using a photodetector, wherein:
at least a portion of the waveguide has a functional layer adapted to bind the analyte;
a plurality of grooves in the optical waveguide form the first grating; and
at least some of the grooves are covered by the functional layer;
when the analyte binds to the functional layer, the binding changes optical characteristics of the waveguide;
the first grating has an optical reflection band characterized by a center wavelength; and
the binding shifts the center wavelength.

11. The method of claim 10, wherein the first grating is a Bragg grating.

12. The method of claim 10, further comprising
transmitting light through one or more additional optical waveguides, each having a grating; and
measuring the transmitted light using a plurality of photodetectors, wherein:
each grating has an optical reflection band characterized by a center wavelength; and
at least two gratings have different reflection bands.

13. The method of claim 12, further comprising routing light via an arrayed waveguide grating (AWG) having an input port and two or more output ports coupled to the two or more optical waveguides, wherein, for each optical waveguide, the AWG is adapted to route light having a corresponding center wavelength from the input port to the output port coupled to said optical waveguide.

14. The method of claim 12, wherein at least two optical waveguides have different functional layers adapted to bind different analytes.

15. The method of claim 10, wherein the optical waveguide is a part of one arm of a Mach-Zehnder interferometer (MZI).

16. The method of claim 15, wherein:
the optical waveguide has a second grating; and
the first and second gratings form an optical resonator.

17. The method of claim 16, wherein:
a section of the optical waveguide between the first and second gratings is covered by the functional layer;
the binding changes a differential phase shift in the MZI; and
measuring the transmitted light comprises measuring the differential phase shift.

18. A device, comprising a Mach-Zehnder interferometer (MZI) having two arms, wherein:
one arm has an optical resonator; and
a section of the resonator has a functional layer adapted to bind an analyte, wherein the optical characteristics of the resonator change, when the analyte binds to the functional layer.

19. The device of claim 18, wherein:
two Bragg gratings form the optical resonator;
the section having the functional layer is located between the gratings; and
the binding changes a differential phase shift in the MZI.

20. The device of claim 18, wherein the optical resonator is formed by two gratings adapted to couple light in and out of the optical resonator and to generate multiple round trips of the light within the resonator.

21. A device, comprising an optical waveguide having a first grating, wherein:
at least a portion of the waveguide has a functional layer adapted to bind an analyte;
when the analyte binds to the functional layer, the binding changes optical characteristics of the waveguide;
the device further comprises one or more other optical waveguides, each having a grating, wherein:
each grating has an optical reflection band characterized by a center wavelength; and
at least two gratings have different reflection bands; and
the device further comprises an arrayed waveguide grating (AWG) having an input port and two or more output ports coupled to the two or more optical waveguides, wherein, for each optical waveguide, the AWG is adapted to route light having a corresponding center wavelength from the input port to the output port coupled to said optical waveguide.

22. The device of claim 21, wherein the AWG and the two or more optical waveguides are implemented in a single integrated device.

23. The device of claim 21, wherein at least two optical waveguides have different functional layers adapted to bind different analytes.

24. A method for detecting an analyte, comprising:
transmitting light through an optical waveguide having a first grating;
measuring the transmitted light using a photo-detector, wherein:
at least a portion of the waveguide has a functional layer adapted to bind the analyte; and
when the analyte binds to the functional layer, the binding changes optical characteristics of the waveguide;
transmitting light through one or more other optical waveguides, each having a grating;
measuring the transmitted light using a plurality of photodetectors, wherein:
each grating has an optical reflection band characterized by a center wavelength; and
at least two gratings have different reflection bands; and
routing light via an arrayed waveauide grating (AWG) having an input port and two or more output ports coupled to the two or more optical waveguides, wherein, for each optical waveguide, the AWG is adapted to route light having a corresponding center wavelength from the input port to the output port coupled to said optical waveguide.

25. The method of claim 24, wherein at least two optical waveguides have different functional layers adapted to bind different analytes.

26. A device, comprising an optical waveguide having a first grating, wherein:
at least a portion of the waveguide has a functional layer adapted to bind an analyte;
when the analyte binds to the functional layer, the binding changes optical characteristics of the waveguide; and
the device comprises a Mach-Zehnder interferometer (MZI) having two arms, wherein one arm includes the optical waveguide, wherein:
the optical waveguide has a second grating; and
the first and second gratings form an optical resonator.

27. The device of claim 26, wherein the first and second gratings are adapted to couple light in and out of the optical resonator and to generate multiple round trips of the light within the resonator.

28. The device of claim 26, wherein:
a section of the optical waveguide between the first and second gratings has the functional layer; and
the binding changes a differential phase shift in the MZI.

29. A method for detecting an analyte, comprising:
transmitting light through an optical waveguide having a first grating; and
measuring the transmitted light using a photo-detector, wherein:
at least a portion of the waveguide has a functional layer adapted to bind the analyte;
the optical waveguide is a part of one arm of a Mach-Zehnder interferometer (MZI);
the optical waveguide has a second grating;
the first and second gratings form an optical resonator; and
when the analyte binds to the functional layer, the binding changes optical characteristics of the waveguide.

30. The method of claim 29, wherein the first and second gratings are adapted to couple light in and out of the optical resonator and to generate multiple round trips of the light within the resonator.

31. The method of claim 29, wherein:
a section of the optical waveguide between the first and second gratings is covered by the functional layer;
the binding changes a differential phase shift in the MZI; and
measuring the transmitted light comprises measuring the differential phase shift.

32. A device, comprising an optical waveguide having a first grating, wherein:
at least a portion of the waveguide has a functional layer adapted to bind an analyte;
when the analyte binds to the functional layer, the binding changes optical characteristics of the waveguide; and
the device further comprises one or more other optical waveguides, each having a grating, wherein:
each grating has an optical reflection band characterized by a center wavelength;
at least two gratings have different reflection bands; and
at least two optical waveguides have different functional layers adapted to bind different analytes.

33. A method for detecting an analyte, comprising:
transmitting light through an optical waveguide having a first grating;
measuring the transmitted light using a photo-detector, wherein:
at least a portion of the waveguide has a functional layer adapted to bind the analyte; and
when the analyte binds to the functional layer, the binding changes optical characteristics of the waveguide;
transmitting light through one or more other optical waveguides, each having a grating; and
measuring the transmitted light using a plurality of photo-detectors, wherein:
each grating has an optical reflection band characterized by a center wavelength;
at least two gratings have different reflection bands; and
at least two optical waveguides have different functional layers adapted to bind different analytes.

34. A device, comprising:
an optical waveguide having a first grating; and
a Mach-Zehnder interferometer (MZI) having two arms, wherein:
at least a portion of the waveguide has a functional layer adapted to bind an analyte;
a plurality of grooves in the optical waveguide form the first grating;
at least some of the grooves are covered by the functional layer;
when the analyte binds to the functional layer, the binding changes optical characteristics of the waveguide; and
one arm includes the optical waveguide.

35. The device of claim 34, wherein:
the optical waveguide has a second grating; and
the first and second gratings form an optical resonator.

36. The device of claim 35, wherein:
a section of the optical waveguide between the first and second gratings has the functional layer; and
the binding changes a differential phase shift in the MZI.

37. A method for detecting an analyte, comprising:
transmitting light through an optical waveguide having a first grating; and measuring the transmitted light using a photo-detector, wherein:
at least a portion of the waveguide has a functional layer adapted to bind the analyte;
a plurality of grooves in the optical waveguide form the first grating; and
at least some of the grooves are covered by the functional layer;
when the analyte binds to the functional layer, the binding changes optical characteristics of the waveguides; and
the optical waveguide is a part of one arm of a Mach-Zehnder interferometer (MZI).

38. The method of claim 37, wherein:
the optical waveguide has a second grating; and
the first and second gratings form an optical resonator.

39. The method of claim 38, wherein:
a section of the optical waveguide between the first and second gratings is covered by the functional layer;
the binding changes a differential phase shift in the MZI; and,
measuring the transmitted light comprises measuring the differential phase shift.

* * * * *

UNITED STATES PATENT AND TRADEMARK OFFICE
CERTIFICATE OF CORRECTION

PATENT NO. : 7,212,693 B2 Page 1 of 1
APPLICATION NO. : 10/743253
DATED : May 1, 2007
INVENTOR(S) : Dustin W. Carr, Ho Bun Chan and Alex T. Tran It is certified that error appears in the above-identified patent and that said Letters Patent is hereby corrected as shown below:

On the Title Page, Item (56) insert --Duveneck et al. US 2003/0108291--
In References Cited, replace "Dotsen ko" with --Dotsenko--.
In References Cited, replace "Sequola" with --Sequoia--.
In References Cited, replace "vol. 2 or 2" with --vol. 2 of 2--.
In References Cited, replace "Blosensor" with --Biosensor--.
In column 6, line 63, replace "waveauide" with --waveguide--

Signed and Sealed this

Thirty-first Day of July, 2007

JON W. DUDAS
*Director of the United States Patent and Trademark Office*